United States Patent [19]

Förster et al.

[11] Patent Number: 4,791,208
[45] Date of Patent: Dec. 13, 1988

[54] NOVEL 5-HALOGENOALKYL-1,3,4-THIADIAZOL-2-YLOXYACETAMIDE HERBICIDES AND FUNGICIDES

[75] Inventors: Heinz Förster; Hans-Joachim Diehr; Fritz Maurer, all of Wuppertal; Erich Klauke, Odenthal; Ludwig Eue, Leverkusen; Hans-Joachim Santel, Cologne; Robert R. Schmidt, Bergisch-Gladbach; Paul Reinecke, Leverkusen; Gerd Hänssler, Leverkusen, all of Fed. Rep. of Germany

[73] Assignee: Bayer Aktiengesellschaft, Leverkusen, Fed. Rep. of Germany

[21] Appl. No.: 83,556

[22] Filed: Aug. 7, 1987

Related U.S. Application Data

[62] Division of Ser. No. 684,567, Dec. 21, 1984, Pat. No. 4,708,731.

[30] Foreign Application Priority Data

Jan. 4, 1984 [DE] Fed. Rep. of Germany ....... 3400168

[51] Int. Cl.$^4$ .......................................... C07D 285/12
[52] U.S. Cl. .................................................. 548/136
[58] Field of Search .......................................... 548/136

[56] References Cited

U.S. PATENT DOCUMENTS

| 2,516,402 | 7/1950 | McBee | 546/345 |
| 4,528,379 | 7/1985 | Cölln | 546/209 |
| 4,549,899 | 10/1985 | Forster | 71/90 |

FOREIGN PATENT DOCUMENTS

| 0018497 | 11/1980 | European Pat. Off. . |
| 0094541 | 11/1983 | European Pat. Off. . |
| 2526308 | 12/1976 | Fed. Rep. of Germany . |
| 3004326 | 8/1981 | Fed. Rep. of Germany . |
| 3218482 | 11/1983 | Fed. Rep. of Germany . |

OTHER PUBLICATIONS

Pavlath, Aromatic Fluorine Compounds, pp. 44-47, 578-579 (1962).

Primary Examiner—Robert Gerstl
Attorney, Agent, or Firm—Sprung Horn Kramer & Woods

[57] ABSTRACT

5-Halogenoalkyl-1,3,4-thiadiazol-2-yloxyacetamides of the formula

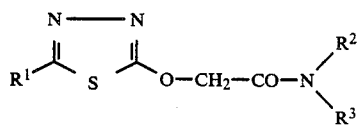

in which
  $R^1$ is halogenoalkyl, with the exception of trifluoromethyl, and
  $R^2$ and $R^3$ each independently is hydrogen, alkyl, alkenyl, alkinyl, in each case optionally substituted cycloalkyl or cycloalkenyl, halogenoalkyl, alkoxyalkyl, alkoxyalkylenoxy, alkoxy, aralkyl or optionally substituted aryl, or
  $R^2$ and $R^3$, together with the nitrogen atom to which they are bonded, form an optionally substituted heterocyclic radical which can contain further hetero-atoms, which possess herbicidal and fungicidal activity. The intermediates 5-chlorodifluoromethyl- and 5-dichlorofluoromethyl-2-chloro-1,3,4- thiadiazole are also new.

3 Claims, No Drawings

NOVEL 5-HALOGENOALKYL-1,3,4-THIADIAZOL-2-YLOXYACETAMIDE HERBICIDES AND FUNGICIDES

This is a division of application Ser. No. 684,567 filed Dec. 21, 1984 now U.S. Pat. No. 4,708,731.

The invention relates to 5-halogenoalkyl-1,3,4-thiadiazol-2-yloxyacetamides, several processes for their preparation and their use as herbicides and fungicides.

It is already known that 5-trifluoromethyl-1,3,4-thiadiazol-2-yloxyacetamides, such as, for example, N-ethyl-N-(3-methylphenyl)-5-trifluoromethyl-1,3,4-thiadiazol-2-yloxyacetamide, N-benzyl-N-methyl-5-trifluoromethyl-1,3,4-thiadiazol-2-yloxyacetamide or N-methyl-N-phenyl-5-trifluoromethyl-1,3,4-thiadiazol-2-yloxyacetamide, have herbicidal properties (application Ser. No. 490,900, filed May 2, 1983, now pending, corresponding to German published specification DOS No. 3,218,482 and DOS No. 3,004,326.

However, their herbicidal activity against harmful plants and also their tolerance towards important crop plants is not always completely satisfactory in all fields of use. Nothing is known of a fungicidal action of this class of substance.

New 5-halogenoalkyl-1,3,4-thiadiazol-2-yloxyacetamides of the general formula (I)

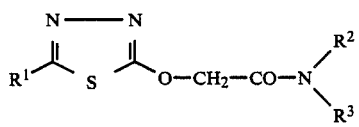

in which
R$^1$ represents halogenoalkyl, with the exception of trifluoromethyl, and
R$^2$ and R$^3$ independently of one another represent hydrogen, alkyl, alkenyl, alkinyl, in each case optionally substituted cycloalkyl or cycloalkenyl, halogenoalkyl, alkoxyalkyl, alkoxyalkylenoxy, alkoxy, aralkyl or optionally substituted aryl, or
R$^2$ and R$^3$, together with the nitrogen atom to which they are bonded, represent an optionally substituted saturated or unsaturated heterocyclic radical, which can contain further hetero-atoms, have been found.

It has furthermore been found that the new 5-halogenoalkyl-1,3,4-thiadiazol-2-yloxyacetamides of the general formula (I)

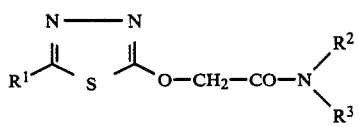

in which
R$^1$ represents halogenoalkyl, with the exception of trifluoromethyl, and
R$^2$ and R$^3$ independently of one another represent hydrogen, alkyl, alkenyl, alkinyl, in each case optionally substituted cycloalkyl or cycloalkenyl, halogenoalkyl, alkoxyalkyl, alkoxyalkylenoxy, alkoxy, aralkyl or optionally substituted aryl, or
R$^2$ and R$^3$, together with the nitrogen atom to which they are bonded, represent an optionally substituted saturated or unsaturated heterocyclic radical which can contain further hetero-atoms, are obtained by a process in which (a) 5-halogenoalkyl-1,3,4-thiadiazole derivatives of the formula (II)

in which
R$^1$ has the abovementioned meaning and
A represents an electron-withdrawing leaving group, are reacted with hydroxyacetamides of the formula (III)

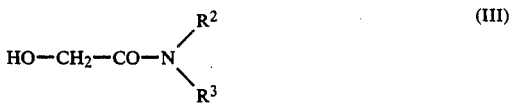

in which
R$^2$ and R$^3$ have the abovementioned meaning, if appropriate in the presence of a diluent and if appropriate in the presence of an acid-binding agent, and if appropriate in the presence of a phase transfer catalyst or in which (b) hydrazine-thiocarboxylic acid O-carbamoylmethyl esters of the formula (IV)

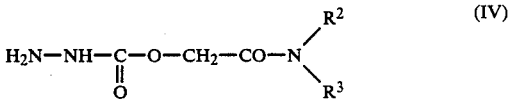

in which
R$^2$ and R$^3$ have the abovementioned meaning, are reacted with halogenocarboxylic acid anhydrides of the formula (V)

in which
R$^1$ has the abovementioned meaning, if appropriate in the presence of a diluent, or in which (c) N'-acyl-hydrazine-N-thiocarboxylic acid O-carbamoylmethyl esters of the formula (VI)

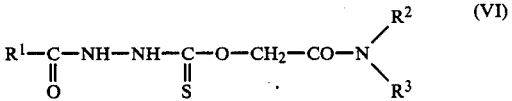

in which
R$^1$, R$^2$ and R$^3$ have the abovementioned meaning, are cyclized with concentrated mineral acids.

Finally, it has been found that the new 5-halogenoalkyl-1,3,4-thiadiazol-2-yloxyacetamides of the general formula (I) have herbicidal properties, in particular selective herbicidal properties, and fungicidal properties.

Surprisingly, the new 5-halogenoalkyl-1,3,4-thiadiazol-2-yloxyacetamides of the formula (I), besides having an improved herbicidal potency against harmful plants, also have a higher tolerance towards important crop plants than the 5-trifluoromethyl-1,3,4-thiadiazol2-yloxyacetamides which are known from the prior art and are closely related compounds chemically and from the point of view of their action.

Formula (I) provides a general definition of the 5-halogenoalkyl-1,3,4-thiadiazol-2-yloxyacetamides according to the invention.

Preferred compounds of the formula (I) are those in which $R^1$ represents straight-chain or branched halogenoalkyl with up to 8 carbon atoms and up to 17 halogen atoms, with the exception of the trifluoromethyl radical, and $R^2$ and $R^3$ independently of one another represent hydrogen, straight-chain or branched alkyl with 1 to 8 carbon atoms, straight-chain or branched alkenyl or alkinyl with in each case 2 to 8 carbon atoms, cycloalkyl or cycloalkenyl, with in each case 3 to 7 carbon atoms and in each case optionally mono- or poly-substituted by identical or different substituents (possible substituents being, in particular, alkyl radicals with 1 to 4 carbon atoms), in each case straight-chain or branched alkoxy, alkoxyalkylenoxy or alkoxyalkyl with in each case 1 to 8 carbon atoms in the individual alkyl or alkylene parts, halogenoalkyl with 1 to 8 carbon atoms and 1 to 5 halogen atoms (in particular fluorine, chlorine and bromine), aralkyl with 6 to 10 carbon atoms in the aryl part and 1 or 2 carbon atoms in the alkyl part, or aryl which has 6 to 10 carbon atoms and is optionally mono- or poly-substituted by identical or different substituents, possible substituents being: halogen, straight-chain or branched alkyl, alkoxy and alkylthio with in each case 1 to 4 carbon atoms, halogenoalkyl, halogenoalkoxy and halogenoalkylthio with in each case 1 to 2 carbon atoms and 1 to 5 halogen atoms (in particular fluorine, chlorine and bromine) and nitro, or $R^2$ and $R^3$, together with the nitrogen atom to which they are bonded, represent a saturated or unsaturated 5-membered to 7-membered heterocyclic radical which is optionally mono- or polysubstituted by identical or different substituents and can contain up to 2 further hetero-atoms, in particular nitrogen and oxygen, possible substituents being: straight-chain or branched alkyl with 1 to 6 carbon atoms, also in the form of a fused-on ring system, aryl with 6 to 10 carbon atoms, also in the form of a fused-on ring system, and dioxyalkylene with 2 or 3 to carbon atoms. Particularly preferred compounds of the formula (I) are those
in which $R^1$ represents chloromethyl, dichloromethyl, trichloromethyl, fluoromethyl, difluoromethyl, chlorofluoromethyl, chlorodifluoromethyl, dichlorofluoromethyl, 1-chloroethyl, 2-chloroethyl, 1,2-dichloroethyl, 2,2,2-trichloroethyl, pentachloroethyl, pentafluoroethyl, 1-bromoethyl, 2-bromoethyl, 2,2,2-tribromoethyl, 1-chloropropyl, 2-chloropropyl, 3-chloropropyl, 1,2-dichloropropyl, 1,2,3-trichloropropyl, heptafluoropropyl, nonafluorobutyl, dichlorobutyl, difluorobutyl, difluorochlorobutyl or dichlorofluorobutyl and $R^2$ and $R^3$ independently of one another represent hydrogen, straight-chain or branched alkyl with 1 to 6 carbon atoms, straight-chain or branched alkenyl or alkinyl with in each case 2 to 6 carbon atoms, cycloalkyl or cycloalkenyl which has 5 to 7 carbon atoms and is optionally mono-, di- or tri-substituted by identical or different substituents from the group comprising methyl and ethyl, in each case straight-chain or branched alkoxy, alkoxyalkylenoxy or alkoxyalkyl with in each case 1 to 6 carbon atoms in the individual alkyl parts, halogenoalkyl with 1 to 6 carbon atoms and 1 to 5 halogen atoms, (in particular fluorine, bromine and chlorine), benzyl, or phenyl which is optionally mono-, di- or tri-substituted by identical or different substituents, particularly preferred substituents being: methyl, ethyl, methoxy, methylthio, trifluoromethyl, trifluoromethoxy, trifluoromethylthio, fluorine, chlorine and nitro, or $R^2$ and $R^3$, together with the nitrogen atom to which they are bonded, represent the following heterocyclic radicals which are optionally mono-, di- or tri-substituted by identical or different substituents:

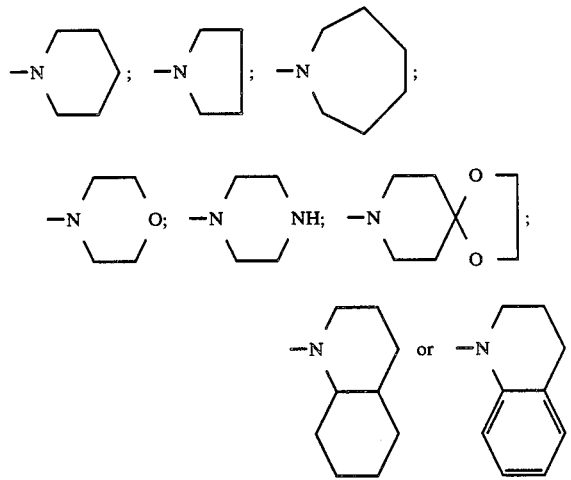

particularly preferred substituents being: methyl, ethyl and phenyl.

The following compounds of the general formula (I) may be mentioned specifically, in addition to the compounds mentioned in the preparation examples:

TABLE 1

| $R^1$ | $R^2$ | $R^3$ |
|---|---|---|
| Cl₂CH— | CH₃ | (phenyl) |

(formula (I) shown above table: N—N ring with $R^1$, S, O—CH₂—CO—N($R^2$)($R^3$))

TABLE 1-continued $$\underset{R^1}{\overset{N\overline{\quad\quad}N}{\diagdown\!\!\diagup\!\!\diagdown\!\!\diagup}}\underset{S}{\phantom{x}}\underset{O-CH_2-CO-N}{\phantom{xx}}\overset{R^2}{\underset{R^3}{\diagdown\diagup}}$$ (I)

| R¹ | R² | R³ |
|---|---|---|
| Cl₂CH— | —CH₂—CH₂—CH₂—CH₂—CH₂—CH₂— | |
| Cl₂CH— | CH₃ | 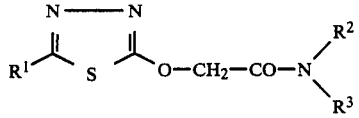 (3-CF₃-C₆H₄—) |
| Cl₂CH— | CH₃ | 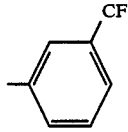 (4-Cl-C₆H₄—) |
| Cl₂CH— | C₂H₅ | C₂H₅ |
| Cl₂CH— | n-C₃H₇ | n-C₃H₇ |
| Cl₂CH— | CH₃ | CH₂=CH—CH₂— |
| Cl₂CH— | CH₂=CH—CH₂— | CH₂=CH—CH₂— |
| Cl₂CH— | CH₃ | 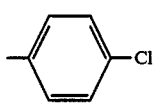 (cyclohexenyl) |
| Cl₂CH— | CH₃ | n-C₄H₉ |
| Cl₂CH— | OCH₃ | s-C₄H₉ |
| Cl₂CH— | C₂H₅—O—CH₂—CH₂—O— | i-C₃H₇ |
| Cl₂CH— | —CH₂—CH₂—CH₂—CH₂—CH— <br>                                          CH₃ | |
| Cl₂CH— | —CH₂—CH₂—CH₂—CH₂—CH— <br>                                          C₂H₅ | |
| Cl₂CH— | —CH₂—CH₂—CH₂—CH—CH₂— <br>                                   CH₃ | |
| Cl—CH₂— | CH₃ | C₆H₅ |
| Cl—CH₂— | C₂H₅ | C₂H₅ |
| Cl—CH₂— | CH₂ | CH₂=CH—CH₂— |
| Cl—CH₂— | CH₂=CH—CH₂— | CH₂=CH—CH₂— |
| Cl—CH₂— | n-C₃H₇ | n-C₃H₇ |
| Cl—CH₂— | CH₃ | n-C₄H₉ |
| Cl—CH₂— | CH₃O | s-C₄H₉ |
| Cl—CH₂— | CH₃O—CH₂— | s-C₄H₉ |
| Cl—CH₂— | n-C₄H₉ | n-C₄H₉ |
| Cl—CH₂— | C₂H₅ | i-C₃H₇ |
| Cl—CH₂— | C₂H₅—O—CH₂—CH₂—O— | i-C₃H₇ |
| Cl—CH₂— | CH₃ | 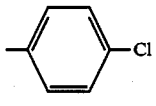 (4-Cl-C₆H₄—) |
| Cl—CH₂— | CH₃ | 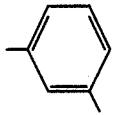 (4-CF₃-C₆H₄—) |

TABLE 1-continued $$\underset{R^1}{\overset{N\!=\!\!=\!\!N}{\underset{S}{\bigvee}}}\!\!\!\!\!\!\!\!\!\!\!\!\!\!\!\!\!\!\overset{}{\underset{}{\bigvee}}\!\!\!\!\!\!\!\!\!O\!-\!CH_2\!-\!CO\!-\!N\!\!\overset{R^2}{\underset{R^3}{\diagdown}}$$ (I)

| $R^1$ | $R^2$ | $R^3$ |
|---|---|---|
| $Cl-CH_2-$ | $CH_3$ |  |
| $Cl-CH_2-$ | $-CH_2-CH_2-CH_2-CH_2-CH_2-$ | |
| $Cl-CH_2-$ | $-CH_2-CH_2-CH_2-CH_2-CH_2-CH_2-$ | |
| $Cl-CH_2-$ | $-\underset{\underset{CH_3}{\vert}}{CH}-CH_2-CH_2-CH_2-CH_2-$ | |
| $Cl-CH_2-$ | $-\underset{\underset{C_2H_5}{\vert}}{CH}-CH_2-CH_2-CH_2-CH_2-$ | |
| $Cl-CH_2-$ | $-CH_2-\underset{\underset{CH_3}{\vert}}{CH}-CH_2-CH_2-CH_2-$ | |
| $Cl-CH_2-$ | $-CH_2-CH_2-\underset{\underset{CH_3}{\vert}}{CH}-CH_2-CH_2-$ | |
| $Cl_3C-$ | $CH_3$ | $C_6H_5$ |
| $Cl_3C-$ | $C_2H_5$ | $n\text{-}C_3H_7$ |
| $Cl_3C-$ | $CH_2$ | $CH_2=CH-CH_2-$ |
| $Cl_3C-$ | $CH_2=CH-CH_2-$ | $CH_2=CH-CH_2-$ |
| $Cl_3C-$ | $n\text{-}C_3H_7$ | $n\text{-}C_3H_7$ |
| $Cl_3C-$ | $CH_3$ | $n\text{-}C_4H_9$ |
| $Cl_3C-$ | $CH_3O$ | $s\text{-}C_4H_9$ |
| $Cl_3C-$ | $CH_3O-CH_2-$ | $s\text{-}C_4H_9$ |
| $Cl_3C-$ | $n\text{-}C_4H_9$ | $n\text{-}C_4H_9$ |
| $Cl_3C-$ | $C_2H_5$ | $i\text{-}C_3H_7$ |
| $Cl_3C-$ | $C_2H_5-O-CH_2-CH_2-O-$ | $i\text{-}C_3H_7$ |
| $Cl_3C-$ | $CH_3$ | 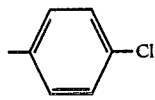 |
| $Cl_3C-$ | $CH_3$ | 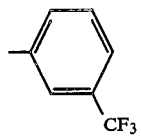 |
| $Cl_3C-$ | $CH_3$ |  |
| $Cl_3C-$ | $-CH_2-CH_2-CH_2-CH_2-CH_2-$ | |
| $Cl_3C-$ | $-CH_2-CH_2-CH_2-CH_2-CH_2-CH_2-$ | |
| $Cl_3C-$ | $-\underset{\underset{CH_3}{\vert}}{CH}-CH_2-CH_2-CH_2-CH_2-$ | |
| $Cl_3C-$ | $-\underset{\underset{C_2H_5}{\vert}}{CH}-CH_2-CH_2-CH_2-CH_2-$ | |
| $Cl_3C-$ | $-CH_2-\underset{\underset{CH_3}{\vert}}{CH}-CH_2-CH_2-CH_2-$ | |

TABLE 1-continued $$\underset{R^1}{\overset{N=N}{\diagdown}}\underset{S}{\diagup}\underset{}{\overset{}{\diagdown}}\underset{O-CH_2-CO-N}{\overset{}{\diagup}}\overset{R^2}{\underset{R^3}{\diagdown}} \quad (I)$$

| $R^1$ | $R^2$ | $R^3$ |
|---|---|---|
| $Cl_3C-$ | $-CH_2-CH_2-\underset{\underset{CH_3}{\|}}{CH}-CH_2-CH_2-$ | |
| $FCH_2-$ | $CH_3$ | $C_6H_5$ |
| $FCH_2-$ | $C_2H_5$ | $C_2H_5$ |
| $FCH_2-$ | $CH_2$ | $CH_2=CH-CH_2-$ |
| $FCH_2-$ | $CH_2=CH-CH_2-$ | $CH_2=CH-CH_2-$ |
| $FCH_2-$ | $n-C_3H_7$ | $n-C_3H_7$ |
| $FCH_2-$ | $CH_3$ | $n-C_4H_9$ |
| $FCH_2-$ | $CH_3O$ | $s-C_4H_9$ |
| $FCH_2-$ | $CH_3O-CH_2-$ | $s-C_4H_9$ |
| $FCH_2-$ | $n-C_4H_9$ | $n-C_4H_9$ |
| $FCH_2-$ | $C_2H_5$ | $i-C_3H_7$ |
| $FCH_2-$ | $C_2H_5-O-CH_2-CH_2-O-$ | $i-C_3H_7$ |
| $FCH_2-$ | $CH_3$ | 4-Cl-C$_6$H$_4$- |
| $FCH_2-$ | $CH_3$ | 3-CF$_3$-C$_6$H$_4$- |
| $FCH_2-$ | $CH_3$ | cyclohexenyl |
| $FCH_2-$ | $-CH_2-CH_2-CH_2-CH_2-CH_2-$ | |
| $FCH_2-$ | $-CH_2-CH_2-CH_2-CH_2-CH_2-CH_2-$ | |
| $FCH_2-$ | $-\underset{\underset{CH_3}{\|}}{CH}-CH_2-CH_2-CH_2-CH_2-$ | |
| $FCH_2-$ | $-\underset{\underset{C_2H_5}{\|}}{CH}-CH_2-CH_2-CH_2-CH_2-$ | |
| $FCH_2$ | $-CH_2-\underset{\underset{CH_3}{\|}}{CH}-CH_2-CH_2-CH_2-$ | |
| $FCH_2-$ | $-CH_2-CH_2-\underset{\underset{CH_3}{\|}}{CH}-CH_2-CH_2-$ | |
| $F_2CH-$ | $CH_3$ | $C_6H_5$ |
| $F_2CH-$ | $C_2H_5$ | $C_2H_5$ |
| $F_2CH-$ | $CH_2$ | $CH_2=CH-CH_2-$ |
| $F_2CH-$ | $CH_2=CH-CH_2-$ | $CH_2=CH-CH_2-$ |
| $F_2CH-$ | $n-C_3H_7$ | $n-C_3H_7$ |
| $F_2CH-$ | $CH_3$ | $n-C_4H_9$ |
| $F_2CH-$ | $CH_3O$ | $s-C_4H_9$ |
| $F_2CH-$ | $CH_3O-CH_2-$ | $s-C_4H_9$ |
| $F_2CH-$ | $n-C_4H_9$ | $n-C_4H_9$ |
| $F_2CH-$ | $C_2H_5-O-CH_2-CH_2-O-$ | $i-C_3H_7$ |
| $F_2CH-$ | $CH_3$ | 4-Cl-C$_6$H$_4$- |

TABLE 1-continued $$\underset{R^1}{\overset{N=N}{\underset{S}{\bigvee}}}O-CH_2-CO-N\overset{R^2}{\underset{R^3}{\bigvee}} \quad (I)$$

| R¹ | R² | R³ |
|---|---|---|
| F₂CH— | CH₃ | —⟨C₆H₄⟩—CF₃ (meta) |
| F₂CH— | CH₃ | cyclohexenyl |
| F₂CH— | —CH₂—CH₂—CH₂—CH₂—CH₂— | |
| F₂CH— | —CH₂—CH₂—CH₂—CH₂—CH₂—CH₂— | |
| F₂CH— | —CH(CH₃)—CH₂—CH₂—CH₂—CH₂— | |
| F₂CH— | —CH(C₂H₅)—CH₂—CH₂—CH₂—CH₂— | |
| F₂CH— | —CH₂—CH(CH₃)—CH₂—CH₂—CH₂— | |
| F₂CH— | —CH₂—CH₂—CH(CH₃)—CH₂—CH₂— | |
| ClFCH— | CH₃ | C₆H₅ |
| ClFCH— | C₂H₅ | C₂H₅ |
| ClFCH— | CH₂=CH—CH₂— | CH₂=CH—CH₂— |
| ClFCH— | CH₂=CH—CH₂— | CH₂=CH—CH₂— |
| ClFCH— | n-C₃H₇ | n-C₃H₇ |
| ClFCH— | CH₃ | n-C₄H₉ |
| ClFCH— | CH₃O | s-C₄H₉ |
| ClFCH— | CH₃O—CH₂— | s-C₄H₉ |
| ClFCH— | n-C₄H₉ | i-C₃H₇ |
| ClFCH— | C₂H₅ | i-C₃H₇ |
| ClFCH— | C₂H₅—O—CH₂—CH₂—O— | i-C₃H₇ |
| ClFCH— | CH₃ | —⟨C₆H₄⟩—Cl (para) |
| ClFCH— | CH₃ | —⟨C₆H₄⟩—CF₃ (para) |
| ClFCH— | CH₃ | cyclohexenyl |
| ClFCH— | —CH₂—CH₂—CH₂—CH₂—CH₂— | |
| ClFCH— | —CH₂—CH₂—CH₂—CH₂—CH₂—CH₂— | |
| ClFCH— | —CH(CH₃)—CH₂—CH₂—CH₂—CH₂— | |

TABLE 1-continued $$\underset{R^1}{\overset{N-N}{\underset{S}{\parallel}}}\overset{}{\underset{O-CH_2-CO-N}{\parallel}}\overset{R^2}{\underset{R^3}{}}\quad (I)$$

| $R^1$ | $R^2$ | $R^3$ |
|---|---|---|
| ClFCH— | —CH(C$_2$H$_5$)—CH$_2$—CH$_2$—CH$_2$—CH$_2$— | |
| ClFCH— | —CH$_2$—CH(CH$_3$)—CH$_2$—CH$_2$—CH$_2$— | |
| ClFCH— | —CH$_2$—CH$_2$—CH(CH$_3$)—CH$_2$—CH$_2$— | |
| ClF$_2$C— | C$_2$H$_5$ | C$_6$H$_5$ |
| ClF$_2$C— | C$_2$H$_5$ | C$_2$H$_5$ |
| ClF$_2$C— | CH$_2$ | CH$_2$=CH—CH$_2$— |
| ClF$_2$C— | CH$_2$=CH—CH$_2$— | CH$_2$=CH—CH$_2$— |
| ClF$_2$C— | n-C$_3$H$_7$ | n-C$_3$H$_7$ |
| ClF$_2$C— | CH$_3$ | n-C$_4$H$_9$ |
| ClF$_2$C— | CH$_3$O | s-C$_4$H$_9$ |
| ClF$_2$C— | CH$_3$O—CH$_2$— | s-C$_4$H$_9$ |
| ClF$_2$C— | n-C$_4$H$_9$ | n-C$_4$H$_9$ |
| ClF$_2$C— | C$_2$H$_5$ | i-C$_3$H$_7$ |
| ClF$_2$C— | C$_2$H$_5$—O—CH$_2$—CH$_2$—O— | i-C$_3$H$_7$ |
| ClF$_2$C— | CH$_3$ | 4-Cl-C$_6$H$_4$— |
| ClF$_2$C— | CH$_3$ | 3-CF$_3$-C$_6$H$_4$— |
| ClF$_2$C— | CH$_3$ | cyclohexenyl |
| ClF$_2$C— | —CH$_2$—CH$_2$—CH$_2$—CH$_2$—CH$_2$— | |
| ClF$_2$C— | —CH$_2$—CH$_2$—CH$_2$—CH$_2$—CH$_2$—CH$_2$— | |
| ClF$_2$C— | —CH(CH$_3$)—CH$_2$—CH$_2$—CH$_2$—CH$_2$— | |
| ClF$_2$C— | —CH(C$_2$H$_5$)—CH$_2$—CH$_2$—CH$_2$—CH$_2$— | |
| ClF$_2$C— | —CH$_2$—CH(CH$_3$)—CH$_2$—CH$_2$—CH$_2$— | |
| ClF$_2$C— | —CH$_2$—CH$_2$—CH(CH$_3$)—CH$_2$—CH$_2$— | |
| Cl$_2$FC— | CH$_3$ | C$_6$H$_5$ |
| Cl$_2$FC— | C$_2$H$_5$ | C$_2$H$_5$ |
| Cl$_2$FC— | CH$_3$ | CH$_2$=CH—CH$_2$— |
| Cl$_2$FC— | CH$_2$=CH—CH$_2$— | CH$_2$=CH—CH$_2$— |
| Cl$_2$FC— | n-C$_3$H$_7$ | n-C$_3$H$_7$ |
| Cl$_2$FC— | CH$_3$ | n-C$_4$H$_9$ |
| Cl$_2$FC— | CH$_3$O | s-C$_4$H$_9$ |
| Cl$_2$FC— | CH$_3$O—CH$_2$— | s-C$_4$H$_9$ |
| Cl$_2$FC— | n-C$_4$H$_9$ | n-C$_4$H$_9$ |
| Cl$_2$FC— | C$_2$H$_5$ | i-C$_3$H$_7$ |

TABLE 1-continued $$\underset{R^1}{\overset{N\text{———}N}{\diagdown}}\underset{S}{\diagup}\overset{}{\diagdown}O-CH_2-CO-N\underset{R^3}{\overset{R^2}{\diagup}} \quad (I)$$

| $R^1$ | $R^2$ | $R^3$ |
|---|---|---|
| $C_2FC-$ | $C_2H_5-O-CH_2-CH_2-O-$ | $i\text{-}C_3H_7$ |
| $Cl_2FC-$ | $CH_3$ |  |
| $Cl_2FC-$ | $CH_3$ | 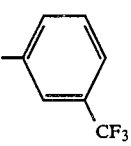 |
| $Cl_2FC-$ | $CH_3$ | 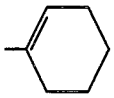 |
| $Cl_2FC-$ | $-CH_2-CH_2-CH_2-CH_2-CH_2-$ | |
| $Cl_2FC-$ | $-CH_2-CH_2-CH_2-CH_2-CH_2-CH_2-$ | |
| $Cl_2FC-$ | $-\underset{\underset{CH_3}{\mid}}{CH}-CH_2-CH_2-CH_2-CH_2-$ | |
| $Cl_2FC-$ | $-\underset{\underset{C_2H_5}{\mid}}{CH}-CH_2-CH_2-CH_2-CH_2-$ | |
| $Cl_2FC-$ | $-CH_2-\underset{\underset{CH_3}{\mid}}{CH}-CH_2-CH_2-CH_2-$ | |
| $Cl_2FC-$ | $-CH_2-CH_2-\underset{\underset{CH_3}{\mid}}{CH}-CH_2-CH_2-$ | |
| $n\text{-}C_3F_7$ | $C_2H_5$ | $C_6H_5$ |
| $n\text{-}C_3F_7$ | $C_2H_5$ | $C_2H_5$ |
| $n\text{-}C_3F_7$ | $CH_2$ | $CH_2=CH-CH_2-$ |
| $n\text{-}C_3F_7$ | $CH_2=CH-CH_2-$ | $CH_2=CH-CH_2-$ |
| $n\text{-}C_3F_7$ | $n\text{-}C_3H_7$ | $n\text{-}C_3H_7$ |
| $n\text{-}C_3F_7$ | $CH_3$ | $n\text{-}C_4H_9$ |
| $n\text{-}C_3F_7$ | $CH_3O$ | $s\text{-}C_4H_9$ |
| $n\text{-}C_3F_7$ | $CH_3O-CH_2-$ | $s\text{-}C_4H_9$ |
| $n\text{-}C_3F_7$ | $n\text{-}C_4H_9$ | $n\text{-}C_4H_9$ |
| $n\text{-}C_3F_7$ | $C_2H_5$ | $i\text{-}C_3H_7$ |
| $n\text{-}C_3F_7$ | $C_2H_5-O-CH_2-CH_2-O-$ | $i\text{-}C_3H_7$ |
| $n\text{-}C_3F_7$ | $CH_3$ | 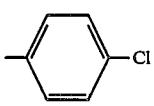 |
| $n\text{-}C_3F_7$ | $CH_3$ | 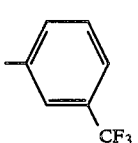 |
| $n\text{-}C_3F_7$ | $CH_3$ | 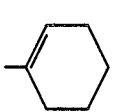 |

TABLE 1-continued $$\underset{R^1}{\overset{N=\!\!=\!\!N}{\underset{S}{\bigvee}}}O-CH_2-CO-\underset{R^3}{\overset{R^2}{N}} \quad (I)$$

| $R^1$ | $R^2$ | $R^3$ |
|---|---|---|
| n-$C_3F_7$ | —$CH_2$—$CH_2$—$CH_2$—$CH_2$—$CH_2$— | |
| n-$C_3F_7$ | —$CH_2$—$CH_2$—$CH_2$—$CH_2$—$CH_2$—$CH_2$— | |
| n-$C_3F_7$ | —CH—$CH_2$—$CH_2$—$CH_2$—$CH_2$—<br>    |<br>   $CH_3$ | |
| n-$C_3F_7$ | —CH—$CH_2$—$CH_2$—$CH_2$—$CH_2$—<br>    |<br>   $C_2H_5$ | |
| n-$C_3F_7$ | —$CH_2$—CH—$CH_2$—$CH_2$—$CH_2$—<br>       |<br>      $CH_3$ | |
| n-$C_3F_7$ | —$CH_2$—$CH_2$—CH—$CH_2$—$CH_2$—<br>           |<br>          $CH_3$ | |
| $CH_3$—CH—<br>    |<br>   Cl | $CH_3$ | $C_6H_5$ |
| $CH_3$—CH—<br>    |<br>   Cl | $C_2H_5$ | $C_2H_5$ |
| $CH_3$—CH—<br>    |<br>   Cl | $CH_2$ | $CH_2$=CH—$CH_2$— |
| $CH_3$—CH—<br>    |<br>   Cl | $CH_2$=CH—$CH_2$— | $CH_2$=CH—$CH_2$— |
| $CH_3$—CH—<br>    |<br>   Cl | n-$C_3H_7$ | n-$C_3H_7$ |
| $CH_3$—CH—<br>    |<br>   Cl | $CH_3$ | n-$C_4H_9$ |
| $CH_3$—CH—<br>    |<br>   Cl | $CH_3O$ | s-$C_4H_9$ |
| $CH_3$—CH—<br>    |<br>   Cl | $CH_3O$—$CH_2$— | s-$C_4H_9$ |
| $CH_3$—CH—<br>    |<br>   Cl | n-$C_4H_9$ | n-$C_4H_9$ |
| $CH_3$—CH—<br>    |<br>   Cl | $C_2H_5$ | i-$C_3H_7$ |
| $CH_3$—CH—<br>    |<br>   Cl | $C_2H_5$—O—$CH_2$—$CH_2$—O— | i-$C_3H_7$ |
| $CH_3$—CH—<br>    |<br>   Cl | $CH_3$ | —C$_6H_4$—Cl (4-Cl-phenyl) |

TABLE 1-continued $$\underset{R^1}{\overset{N\!-\!\!-\!\!-\!N}{\diagdown\!\!\diagup}}\underset{S}{\overset{}{}}\underset{}{\overset{}{}}O\!-\!CH_2\!-\!CO\!-\!N\!\overset{R^2}{\underset{R^3}{\diagup\!\!\!\diagdown}} \quad (I)$$

| R¹ | R² | R³ |
|---|---|---|
| $CH_3-CHCl-$ | $CH_3$ | 3-(CF₃)-phenyl |
| $CH_3-CHCl-$ | $CH_3$ | 1-cyclohexenyl |
| $CH_3-CHCl-$ | $-CH_2-CH_2-CH_2-CH_2-CH_2-$ | |
| $CH_3-CHCl-$ | $-CH_2-CH_2-CH_2-CH_2-CH_2-CH_2-$ | |
| $CH_3-CHCl-$ | $-CH(CH_3)-CH_2-CH_2-CH_2-CH_2-$ | |
| $CH_3-CHCl-$ | $-CH(C_2H_5)-CH_2-CH_2-CH_2-CH_2-$ | |
| $CH_3-CHCl-$ | $-CH_2-CH(CH_3)-CH_2-CH_2-CH_2-$ | |
| $CH_3-CHCl-$ | $-CH_2-CH_2-CH(CH_3)-CH_2-CH_2-$ | |
| $Cl-CH_2-CH_2-$ | $CH_3$ | $C_6H_5$ |
| $Cl-CH_2-CH_2-$ | $C_2H_5$ | $C_2H_5$ |
| $Cl-CH_2-CH_2-$ | $CH_2$ | $CH_2=CH-CH_2-$ |
| $Cl-CH_2-CH_2-$ | $CH_2=CH-CH_2-$ | $CH_2=CH-CH_2-$ |
| $Cl-CH_2-CH_2-$ | $n-C_3H_7$ | $n-C_3H_7$ |
| $Cl-CH_2-CH_2-$ | $CH_3$ | $n-C_4H_9$ |
| $Cl-CH_2-CH_2-$ | $CH_3O$ | $s-C_4H_9$ |
| $Cl-CH_2-CH_2-$ | $CH_3O-CH_2-$ | $s-C_4H_9$ |
| $Cl-CH_2-CH_2-$ | $n-C_4H_9$ | $n-C_4H_9$ |
| $Cl-CH_2-CH_2-$ | $C_2H_5$ | $i-C_3H_7$ |
| $Cl-CH_2-CH_2-$ | $C_2H_5-O-CH_2-CH_2-O-$ | $i-C_3H_7$ |
| $Cl-CH_2-CH_2-$ | $CH_3$ | 4-Cl-phenyl |
| $Cl-CH_2-CH_2-$ | $CH_3$ | 3-(CF₃)-phenyl |
| $Cl-CH_2-CH_2$ | $CH_3$ | 1-cyclohexenyl |
| $Cl-CH_2-CH_2-$ | $-CH_2-CH_2-CH_2-CH_2-CH_2-$ | |
| $Cl-CH_2-CH_2-$ | $-CH_2-CH_2-CH_2-CH_2-CH_2-CH_2-$ | |

TABLE 1-continued $$\underset{R^1}{\overset{N\text{———}N}{\underset{S}{\parallel}\quad\underset{O-CH_2-CO-N}{\parallel}}}\overset{R^2}{\underset{R^3}{}} \quad (I)$$

| $R^1$ | $R^2$ | $R^3$ |
|---|---|---|
| Cl—CH$_2$—CH$_2$— | —CH(CH$_3$)—CH$_2$—CH$_2$—CH$_2$—CH$_2$— | |
| Cl—CH$_2$—CH$_2$— | —CH(C$_2$H$_5$)—CH$_2$—CH$_2$—CH$_2$—CH$_2$— | |
| Cl—CH$_2$—CH$_2$— | —CH$_2$—CH(CH$_3$)—CH$_2$—CH$_2$—CH$_2$— | |
| Cl—CH$_2$—CH$_2$— | —CH$_2$—CH$_2$—CH(CH$_3$)—CH$_2$—CH$_2$— | |
| Cl—CH$_2$—CH$_2$—CH$_2$— | CH$_3$ | C$_6$H$_5$ |
| Cl—CH$_2$—CH$_2$—CH$_2$— | C$_2$H$_5$ | C$_2$H$_5$ |
| Cl—CH$_2$—CH$_2$—CH$_2$— | CH$_2$=CH—CH$_2$— | CH$_2$=CH—CH$_2$— |
| Cl—CH$_2$—CH$_2$—CH$_2$— | CH$_2$=CH—CH$_2$— | CH$_2$=CH—CH$_2$— |
| Cl—CH$_2$—CH$_2$—CH$_2$— | n-C$_3$H$_7$ | n-C$_3$H$_7$ |
| Cl—CH$_2$—CH$_2$—CH$_2$— | CH$_3$ | n-C$_4$H$_9$ |
| Cl—CH$_2$—CH$_2$—CH$_2$— | CH$_3$O | s-C$_4$H$_9$ |
| Cl—CH$_2$—CH$_2$—CH$_2$— | CH$_3$O—CH$_2$— | s-C$_4$H$_9$ |
| Cl—CH$_2$—CH$_2$—CH$_2$— | n-C$_4$H$_9$ | n-C$_4$H$_9$ |
| Cl—CH$_2$—CH$_2$—CH$_2$— | C$_2$H$_5$ | i-C$_3$H$_7$ |
| Cl—CH$_2$—CH$_2$—CH$_2$— | C$_2$H$_5$—O—CH$_2$—CH$_2$—O— | i-C$_3$H$_7$ |
| Cl—CH$_2$—CH$_2$—CH$_2$— | CH$_3$ | 4-Cl-C$_6$H$_4$— |
| Cl—CH$_2$—CH$_2$—CH$_2$— | CH$_3$ | 3-CF$_3$-C$_6$H$_4$— |
| Cl—CH$_2$—CH$_2$—CH$_2$— | CH$_3$ | cyclohexen-1-yl |
| Cl—CH$_2$—CH$_2$—CH$_2$— | —CH$_2$—CH$_2$—CH$_2$—CH$_2$—CH$_2$— | |
| Cl—CH$_2$—CH$_2$—CH$_2$— | —CH$_2$—CH$_2$—CH$_2$—CH$_2$—CH$_2$— | |
| Cl—CH$_2$—CH$_2$—CH$_2$— | —CH(CH$_3$)—CH$_2$—CH$_2$—CH$_2$—CH$_2$— | |
| Cl—CH$_2$—CH$_2$—CH$_2$— | —CH(C$_2$H$_5$)—CH$_2$—CH$_2$—CH$_2$—CH$_2$— | |
| Cl—CH$_2$—CH$_2$—CH$_2$— | —CH$_2$—CH(CH$_3$)—CH$_2$—CH$_2$—CH$_2$— | |
| Cl—CH$_2$—CH$_2$—CH$_2$— | —CH$_2$—CH$_2$—CH(CH$_3$)—CH$_2$—CH$_2$— | |
| CH$_3$—CH(Br)— | CH$_3$ | C$_6$H$_5$ |

TABLE 1-continued $$\underset{R^1}{\overset{N\text{---}N}{\underset{S}{\diagdown}}}\overset{}{\underset{}{\diagup}}\text{O}-\text{CH}_2-\text{CO}-\text{N}\overset{R^2}{\underset{R^3}{\diagdown}} \quad (I)$$

| $R^1$ | $R^2$ | $R^3$ |
|---|---|---|
| $CH_3-\underset{Br}{CH}-$ | $C_2H_5$ | $C_2H_5$ |
| $CH_3-\underset{Br}{CH}-$ | $CH_2$ | $CH_2=CH-CH_2-$ |
| $CH_3-\underset{Br}{CH}-$ | $CH_2=CH-CH_2-$ | $CH_2=CH-CH_2-$ |
| $CH_3-\underset{Br}{CH}-$ | $n\text{-}C_3H_7$ | $n\text{-}C_3H_7$ |
| $CH_3-\underset{Br}{CH}-$ | $CH_3$ | $n\text{-}C_4H_9$ |
| $CH_3-\underset{Br}{CH}-$ | $CH_3O$ | $n\text{-}C_4H_9$ |
| $CH_3-\underset{Br}{CH}-$ | $CH_3O-CH_2-$ | $s\text{-}C_4H_9$ |
| $CH_3-\underset{Br}{CH}-$ | $n\text{-}C_4H_9$ | $n\text{-}C_4H_9$ |
| $CH_3-\underset{Br}{CH}-$ | $C_2H_5$ | $i\text{-}C_3H_7$ |
| $CH_3-\underset{Br}{CH}-$ | $C_2H_5-O-CH_2-CH_2-O-$ | $i\text{-}C_3H_7$ |
| $CH_3-\underset{Br}{CH}-$ | $CH_3$ | 4-Cl-phenyl |
| $CH_3-\underset{Br}{CH}-$ | $CH_3$ | 3-$CF_3$-phenyl |
| $CH_3-\underset{Br}{CH}-$ | $CH_3$ | cyclohex-1-enyl |
| $CH_3-\underset{Br}{CH}-$ | $-CH_2-CH_2-CH_2-CH_2-CH_2-$ | |
| $CH_3-\underset{Br}{CH}-$ | $-CH_2-CH_2-CH_2-CH_2-CH_2-CH_2-$ | |
| $CH_3-\underset{Br}{CH}-$ | $-\underset{CH_3}{CH}-CH_2-CH_2-CH_2-CH_2-$ | |

TABLE 1-continued $$\underset{R^1}{\overset{N\underline{\quad\quad}N}{\diagup\diagdown}}\underset{S}{\diagdown}\underset{}{\diagup}O-CH_2-CO-N\overset{R^2}{\underset{R^3}{\diagdown}}\quad (I)$$

| R¹ | R² | R³ |
|---|---|---|
| CH₃—CH(Br)— | —CH(C₂H₅)—CH₂—CH₂—CH₂—CH₂— | |
| CH₃—CH(Br)— | —CH₂—CH(CH₃)—CH₂—CH₂—CH₂— | |
| CH₃—CH(Br)— | —CH₂—CH₂—CH(CH₃)—CH₂—CH₂— | |
| Cl—CH₂—CH(Cl)— | CH₃ | C₆H₅ |
| Cl—CH₂—CH(Cl)— | C₂H₅ | C₂H₅ |
| Cl—CH₂—CH(Cl)— | CH₂ | CH₂=CH—CH₂— |
| Cl—CH₂—CH(Cl)— | CH₂=CH—CH₂— | CH₂=CH—CH₂— |
| Cl—CH₂—CH(Cl)— | n-C₃H₇ | n-C₃H₇ |
| Cl—CH₂—CH(Cl)— | CH₃ | n-C₄H₉ |
| Cl—CH₂—CH(Cl)— | CH₃O | s-C₄H₉ |
| Cl—CH₂—CH(Cl)— | CH₃O—CH₂— | s-C₄H₉ |
| Cl—CH₂—CH(Cl)— | n-C₄H₉ | n-C₄H₉ |
| Cl—CH₂—CH(Cl)— | C₂H₅ | i-C₃H₇ |
| Cl—CH₂—CH(Cl)— | C₂H₅—O—CH₂—CH₂—O— | i-C₃H₇ |
| Cl—CH₂—CH(Cl)— | CH₃ | 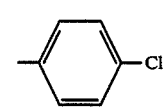 4-Cl-C₆H₄— |
| Cl—CH₂—CH(Cl)— | CH₃ | 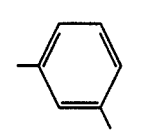 3-CF₃-C₆H₄— |

TABLE 1-continued

| $R^1$ | $R^2$ | $R^3$ |
|---|---|---|
| Cl—CH₂—CH(Cl)— | CH₃ | cyclohexenyl |
| Cl—CH₂—CH(Cl)— | —CH₂—CH₂—CH₂—CH₂—CH₂— | |
| Cl—CH₂—CH(Cl)— | —CH₂—CH₂—CH₂—CH₂—CH₂—CH₂— | |
| Cl—CH₂—CH(Cl)— | —CH(CH₃)—CH₂—CH₂—CH₂—CH₂— | |
| Cl—CH₂—CH(Cl)— | —CH(C₂H₅)—CH₂—CH₂—CH₂—CH₂— | |
| Cl—CH₂—CH(Cl)— | —CH₂—CH(CH₃)—CH₂—CH₂—CH₂— | |
| Cl—CH₂—CH(Cl)— | —CH₂—CH₂—CH(CH₃)—CH₂—CH₂— | |

If, for example, 2-chloro-5-trichloromethyl-1,3,4-thiadiazole and hydroxyacetic acid diethylamide are used as starting substances, the course of reaction in process (a) according to the invention can be represented by the following equation:

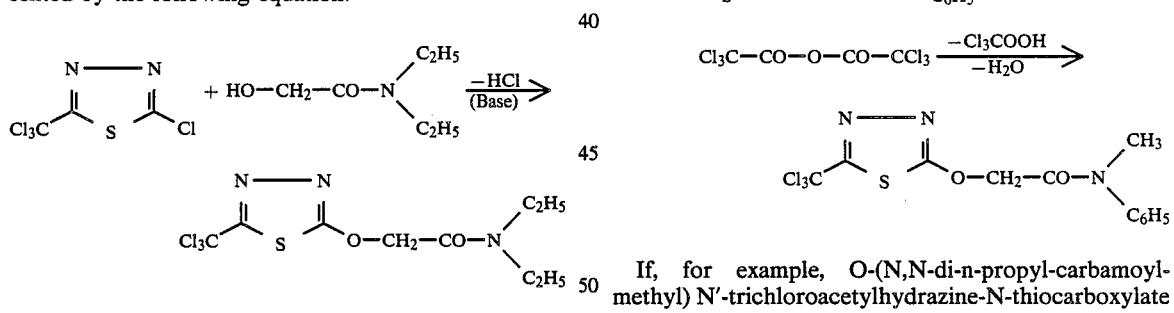

If, for example, O-(N-methyl-N-phenyl-carbamoylmethyl) hydrazine-thiocarboxylate and trichloroacetic anhydride are used as starting substances, the course of the reaction in process (b) according to the invention can be represented by the following equation:

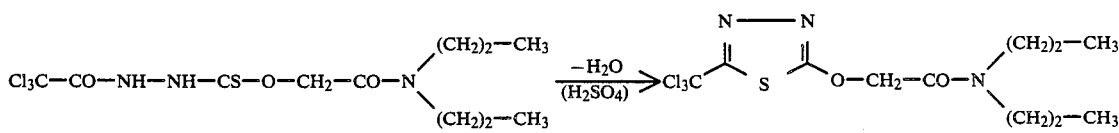

If, for example, O-(N,N-di-n-propyl-carbamoylmethyl) N'-trichloroacetylhydrazine-N-thiocarboxylate and concentrated sulphuric acid are used as starting substances, the course of the reaction in process (c) according to the invention can be represented by the following equation:

Formula (II) provides a general definition of the 5-halogenoalkyl-1,3,4-thiadiazole derivatives required as starting substances for carrying out process (a) according to the invention. In this formula (II), $R^1$ preferably represents those substituents which have already been mentioned as preferred for this radical in the description of the substances of the formula (I) according to the invention. A preferably represents halogen or alkylsulphonyl or aralkylsulphonyl, in particular chlorine, bromine, methylsulphonyl or ethylsulphonyl.

Some of the 5-halogeno-1,3,4-thiadiazole derivatives of the formula (II) are known (compare, for example, Liebigs Ann. Chem. 1980, 1219, DE-OS (German published specification) No. 1,817,069 and U.S. Pat. No. 3,562,284).

The compounds of the formula (II) which are not yet known are obtained in an analogous manner by processes which are known in principle (compare, for example, DE-OS (German published specification) 3,228,147; J. Chem. Soc. 1949, 1918–1923; J. Chem. Soc. 1949, 3311–3315; U.S. Pat. No. 3,260,588; J. Heterocyclic Chem. Vol. 11(3), pages 343–345, 1974).

Formula (III) provides a general definition of the hydroxyacetamides which are furthermore required as starting substances for carrying out process (a) according to the invention. In this formula (III), $R^2$ and $R^3$ preferably represent those radicals which have already been mentioned as preferred for these substituents in the description of the substances of the formula (I) according to the invention. The hydroxyacetamides of the formula (III) are known (compare, for example, European Pat. No. 18,497, European Pat. No. 29,171, DE-OS (German published specification) No. 3,038,598 and DE-OS (German published specification) No. 3,148,839), or they can be obtained in an analogous manner by processes which are known in principle.

Formula (IV) provides a general definition of the hydrazine-thiocarboxylic acid O-carbamoylmethyl esters required as starting substances for carrying out process (b) according to the invention. In this formula (IV), $R^2$ and $R^3$ preferably represent those radicals which have already been mentioned as preferred for these substituents in the description of the substances of the formula (I) according to the invention.

The hydrazine-thiocarboxylic acid O-carbamoylmethyl esters of the formula (IV) are the subject of Ser. No. 684,568, filed on even date herewith (corresponding to German application P No. 34 00 170.0, filed Jan. 4, 1984).

They are obtained either by a process in which O-carbamoylmethyl S-carboxymethyl dithiocarbonates of the formula (VII)

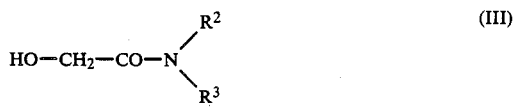

in which $R^2$ and $R^3$ have the abovementioned meaning, are reacted with hydrazine hydrate, if appropriate in the presence of a diluent, such as, for example, water, and if appropriate in the presence of an acid-binding agent, such as, for example, sodium bicarbonate, at temperatures between $-20°$ C. and $+50°$ C., or by a process in which hydroxyacetamides of the formula (III)

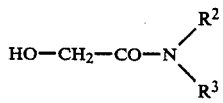

in which $R_2$ and $R^3$ have the abovementioned meaning, are reacted successively in a "one-pot process", first with carbon disulphide in the presence of a base, such as, for example, an alkali metal hydroxide, and then with an alkali metal chloroacetate, such as, for example, sodium chloroacetate, and finally with hydrazine hydrate, if appropriate in the presence of a diluent, such as, for example, water, at temperatures between $0°$ C. and $+60°$ C.

The O-carbamoylmethyl S-carboxymethyl dithiocarbonates of the formula (VII) are likewise not yet known.

They are obtained by a process in which hydroxyacetamides of the formula (III)

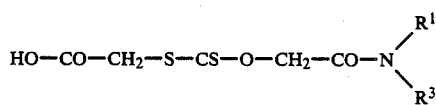

in which $R^2$ and $R^3$ have the abovementioned meaning, are reacted successively in a "one-pot process", first with carbon disulphide in the presence of a base, such as, for example, potassium hydroxide, and then with an alkali metal chloroacetate, such as, for example, sodium chloroacetate, and finally with an acid, such as, for example, hydrochloric acid, if appropriate in the presence of a diluent, such as, for example, water, at temperatures between $0°$ C. and $+60°$ C.

Formula (V) provides a general definition of the halogenocarboxylic acid anhydrides furthermore required as starting substances for carrying out process (b) according to the invention. In this formula (V), $R^1$ preferably represents those radicals which have already been mentioned as preferred for this substituent in the description of the substances of the formula (I) according to the invention.

The halogenocarboxylic acid anhydrides of the formula (V) are generally compounds of organic chemistry.

Formula (VI) provides a general definition of the N'-acyl-hydrazine-N-thiocarboxylic acid O-carbamoylmethyl esters required as starting substances for carrying out process (c) according to the invention. In this formula (VI), $R^1$, $R^2$ and $R^3$ preferably represent those radicals which have already been mentioned as preferred for these substituents in the description of the substances of the formula (I) according to the invention.

The N'-acyl-hydrazine-N-thiocarboxylic acid O-carbamoylmethyl esters of the formula (VI) are the subject of application Ser. No. 684,568, filed on even date herewith (corresponding to German application P No. 34 00 169, filed Jan. 6, 1984.

They are obtained by a process in which either hydrazine-N-thiocarboxylic acid O-carbamoylmethyl esters of the general formula (IV)

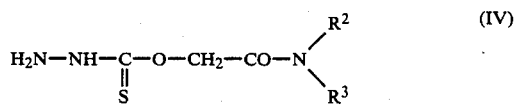

in which $R^2$ and $R^3$ have the abovementioned meaning, are reacted with acylating agents of the formula (VIII)

$$R^1-CO-X \tag{VIII}$$

in which

R[1] has the abovementioned meaning and

X represents halogen or alkoxy, in particular chlorine, bromine, methoxy or ethoxy, if appropriate in the presence of a diluent, such as, for example, dimethylformamide, and if appropriate in the presence of an acid-binding agent, such as, for example, pyridine, at temperatures between −20° C. and +60° C., or in which O-carbamoylmethyl S-carboxymethyl dithiocarbonates of the formula (VII)

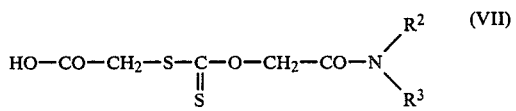

in which $R^2$ and $R^3$ have the abovementioned meaning, are reacted with N-acylhydrazines of the formula (IX)

$$R^1-CO-NH-NH_2 \tag{IX}$$

in which

R[1] has the abovementioned meaning, if appropriate in the presence of a diluent, such as, for example, water, and if appropriate in the presence of an acid-binding agent, such as, for example, sodium bicarbonate, at temperatures between −20° C. and +50° C., or in which hydroxyacetamides of the formula (III)

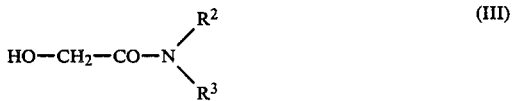

in which $R^2$ and $R^3$ have the abovementioned meaning, are reacted successively in a "one-pot process", first with carbon disulphide in the presence of a base, such as, for example, potassium hydroxide, and then with an alkali metal chloroacetate, such as, for example, sodium chloroacetate, and finally with an N-acylhydrazine of the formula (IX)

$$R^1-CO-NH-NH_2 \tag{IX}$$

in which

R[1] has the abovementioned meaning, if appropriate in the presence of a diluent, such as, for example, water, at temperatures between −20° C. and +60° C.

Acylating agents of the formula (VIII) are generally known compounds of organic chemistry.

The N-acylhydrazines of the formula (IX) are likewise generally known compounds of organic chemistry, or they can be obtained in the generally customary manner by acylation of hydrazines by processes which are known in principle (compare, for example, C. Ferri, 'Reaktionen der organischen Synthese' ('Reactions of Organic Synthesis'), Thieme Verlag Stuttgart 1978, pages 562 and 563).

Possible diluents for process (a) according to the invention are organic or inorganic solvents. Preferred solvents are hydrocarbons, such as toluene or cyclohexane, halogenohydrocarbons, such as methylene chloride, chloroform, dichloroethane or chlorobenzene, ketones, such as acetone or methyl isobutyl ketone, ethers, such as diethyl ether, diisopropyl ether or methyl t-butyl ether, alcohols, such as methanol, ethanol or isopropanol, amides, such as dimethylformamide or dimethylacetamide, sulphoxides, such as dimethylsulphoxide, water or aqueous salt solutions.

Salts which are preferably used here are chlorides or sulphates of alkali metals or alkaline earth metals, such as, for example, sodium chloride, potassium chloride or calcium chloride. Sodium chloride is particularly preferred.

Process (a) according to the invention is preferably carried out using acid-binding agents. Preferred acid-binding agents are strongly basic alkali metal and alkaline earth metal compounds, for example oxides, such as, for example, sodium oxide, potassium oxide, magnesium oxide and calcium oxide, hydroxides, such as, for example, sodium hydroxide, potassium hydroxide, magnesium hydroxide and calcium hydroxide, and/or carbonates, such as, for example, sodium carbonate, potassium carbonate, magnesium carbonate and calcium carbonate.

The addition of 0.01 to 10 percent by weight (based on the hydroxyacetamide of the formula (III) employed) of a phase transfer catalyst may prove to be advantageous in some cases. Examples of such catalysts which may be mentioned are: tetrabutylammonium chloride, tetrabutylammonium bromide, tributylmethylphosphonium bromide, trimethyl-$C_{13}/C_{15}$-alkylammonium chloride, dibenzyl-dimethylammonium methylsulphate, dimethyl-$C_{12}/C_{14}$-alkylbenzylammonium chloride, tetrabutylammonium hydroxide, 18-crown-6, triethylbenzylammonium chloride, trimethylbenzylammonium chloride, tetraethylammonium bromide and tetraethylammonium chloride.

The reaction temperatures can be varied within a substantial range in process (a) according to the invention. They are in general between −50° C. and +100° C., preferably between −20° C. and +100° C.

Process (a) according to the invention is in general carried out under normal pressure, but it can also be carried out under increased or reduced pressure, for example between 0.1 to 10 bar.

For carrying out process (a) according to the invention, in general 0.1 to 10 moles, preferably 0.8 to 1.2 moles, of hydroxyacetamide of the formula (III) and 0.5 to 10 moles, preferably 0.5 to 5 moles, of base are employed per mole of 5-halogenoalkyl-1,3,4-thiadiazole derivative of the formula (II). The sequence of addition of the reactants can be interchanged as desired, and it is also possible to meter all the components simultaneously into the reaction vessel. The reaction procedure can be continuous or discontinuous. Working up is effected in the customary manner.

Possible diluents for carrying out process (b) according to the invention are inert organic solvents. Solvents which are preferably used are aliphatic or aromatic, optionally halogenated hydrocarbons, such as benzine, benzene, toluene, xylene, hexane, cyclohexane, methylene chloride, chloroform, carbon tetrachloride or chlorobenzene, ketones, such as acetone or butanone, nitriles, such as acetonitrile or propionitrile, ethers, such as diethyl ether, dioxane, tetrahydrofuran or diisopropyl ether, esters, such as ethyl acetate, or amides, such as dimethylformamide or hexamethylphosphoric acid triamide.

The reaction temperatures can be varied within a substantial range in carrying out process (b) according to the invention. In general, the reaction is carried out between −30° C. and +30° C., preferably between −10° C. and +20° C.

For carrying out process (b) according to the invention, in general 1 to 5 moles, preferably 1.5 to 3 moles, of halogenocarboxylic acid anhydride of the formula (V) are employed per mole of hydrazinethiocarboxylic acid O-carbamoylmethyl ester of the formula (IV). For working up, excess anhydride of the formula (V) and by-products are removed by treatment with aqueous base, and the reaction product of the formula (I) is isolated by extraction with a suitable water-immiscible solvent. The products are characterized with the aid of their refractive index or melting point.

In principle, all the mineral acids which can customarily be used for such cyclisation reactions are suitable for carrying out process (c) according to the invention. Concentrated sulphuric acid is preferably used.

Process (c) according to the invention is preferably carried out without the addition of a diluent.

The reaction temperatures can be varied within a substantial range in carrying out process (c) according to the invention. In general, the reaction is carried out between −50° C. and +50° C., preferably between −30° C. and +20° C.

For carrying out process (c) according to the invention, in general 5 to 50 moles, preferably 10 to 20 moles, of concentrated sulphuric acid are employed per mole of N'-acyl-hydrazine-N-thiocarboxylic acid O-carbamoyl ester of the formula (VI). For working up, the reaction mixture is diluted with water and the product of the formula (I), which is insoluble in water, is extracted with a suitable organic solvent. The products are characterized with the aid of their refractive index or melting point.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas. Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds of the formula (I) according to the invention also exhibit here, besides a particularly good general herbicidal activity, a significantly improved selectivity for crop plants in important crops and can be used, in particular, for combating weeds in beet, soy beans, cotton and cereals.

The active compounds according to the invention also exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds at the concentrations required for combating plant diseases permits treatment of above-ground parts of plants, of vegetative propagation stock and seeds, and of the soil.

The substances according to the invention can be used here with particularly good success for combating cereal diseases or rice diseases, such as, for example, against the causative organisms *Pyricularia oryzae*, Puccinia recondita, Cochliobolus sativus or Pyrenophora teres, and also against Oomycetes or against the apple scab causative organism (*Venturia inaequalis*).

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperatures and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs; and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethyl-urea, for combating weeds in cereals; 4-amino-3-methyl-6-phenyl-1,2,4-triazin-5(4H)-one for combating weeds in sugar beet and 4-amino-6-(1,1-dimethylethyl)-3-methylthio-1,2,4-triazin-5(4H)-one for combating weeds in soy beans.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, immersion, misting, vaporizing, injecting, forming a slurry, brushing on, dusting, scattering, dry dressing, moist dressing, wet dressing, slurry dressing or encrusting.

When used as herbicides, the active compounds according to the invention can be applied either before or after emergence of the plants.

They can also be incorporated into the soil before sowing.

The amount of active compound used can vary within a substantial range in the case of use as herbicides. It depends essentially on the nature of the desired effect. In general, the amounts used are between 0.01 and 15 kg of active compound per hectare of soil surface, preferably between 0.05 and 20 kg per ha.

When used as fungicides, the active compound concentrations in the use forms can be varied within a substantial range. In the treatment of parts of plants, they are in general between 1 and 0.0001% by weight, preferably between 0.5 and 0.001%.

In the treatment of seed, active compound amounts of 0.001 to 50 g per kilogram of seed, preferably 0.01 to 10 g, are in general required.

For the treatment of soil, active compound concentrations of 0.00001 to 0.1% by weight, preferably 0.0001 to 0.02% by weight, are required at the place of action.

The preparation and use of the active compounds according to the invention can be seen from the following examples.

PREPARATION EXAMPLES

Example 1

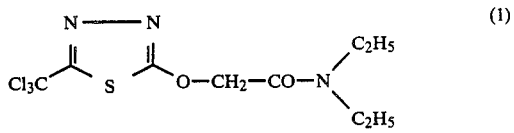

(Process (a))

A solution of 2.4 g (0.06 mole) of sodium hydroxide in 4 ml of water is slowly added to a solution of 6.5 g (0.05 mole) of hydroxyacetic acid diethylamide and 13.8 g (0.05 mole) of 2-chloro-5-trichloromethyl-1,3,4-thiadiazole in 100 ml of toluene at −10° C., with stirring. When the addition has ended, stirring is continued at 0° C. to 5° C. for 12 hours. For working up, the organic phase is washed with water until neutral and concentrated in vacuo and the residue is triturated at 0° C. with petroleum ether. The solid thus obtained is filtered off with suction and dried.

7 g (42% of theory) of N,N-diethyl-5-trichloromethyl-thiadiazol-2-yloxyacetamide of melting point 42° C. are obtained.

Example 2

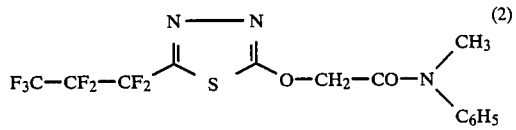

(Process (a))

8.3 g (0.025 mole) of 2-methylsulphonyl-5-heptafluoro-n-propyl-1,3,4-thiadiazole and 4.3 g of hydroxyacetic acid N-methylanilide are added to a suspension of 3.8 g of potassium carbonate and 0.5 g of tetrabutylammonium bromide in 50 ml of acetone at 20° C. When the addition has ended, the mixture is stirred at room temperature for 20 hours, the solvent is distilled off, the residue is taken up in water and the mixture is extracted with 100 ml of ligroin. The combined organic phases are freed from the solvent in vacuo.

9.1 g (87% of theory) of 5- heptafluoro-n-propyl-1,3,4-thiadiazol-2-yloxyacetic acid N-methylanilide are obtained as an oil of refractive index $n_D^{20}$ 1.4662.

PREPARATION OF THE STARTING SUBSTANCE (FOR EXAMPLE 2)

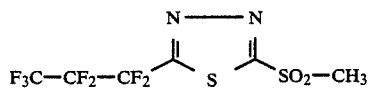

Chlorine is passed into a solution of 35 g (0.11 mole) of 2-heptafluoro-n-propyl-5-methylthio-1,3,4-thiadiazole in 280 ml of acetic acid and 70 ml of water at 5° C. to 10° C. until a yellow solid precipitates. The reaction mixture is subsequently stirred at 30° C. for a further 30 minutes and then extracted with chloroform. The combined chloroform phases are washed with water, dried over sodium sulphate and concentrated in vacuo.

26 g (71% of theory) of 5-heptafluoro-n-propyl-2-methylsulphonyl-1,3,4-thiadiazole of melting point 62° C. are obtained.

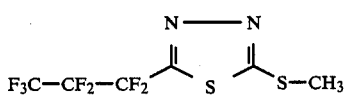

43 g (0.2 mole) of perfluorobutyric acid are added to a solution of 13.8 g (0.1 mole) of potassium carbonate in 20 ml of water at 20° C., the mixture is stirred at room temperature for 15 minutes, 200 ml of toluene are added and the water is distilled off. 24.2 g (0.2 mole) of hydrazine-dithiocarboxylic acid methylester are added to the suspension thus obtained, followed by 39 g (0.25 mole) of phosphorous oxychloride at 50° C. to 60° C. When the addition has ended, stirring is continued at 70° C. to 80° C. for 2 hours, the resulting reaction mixture is poured onto ice-water, the organic phase is separated off, washed with water until neutral and dried over sodium sulphate and the solvent is removed in vacuo.

49 g (82% of theory) of 5-heptafluoro-n-propyl-2-methylthio-1,3,4-thiadiazole are obtained as a yellow oil.

Example 3

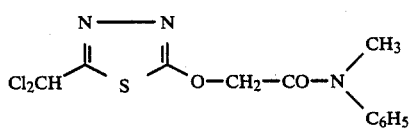

(Process (b))

28.8 g (0.12 mole) of dichloroacetic acid anhydride are added to a mixture of 11.95 g (2.25 mole) of O-(N-methyl-N-phenylcarbamoyl-methyl) hydrazine-thiocarboxylate and 125 ml of diethyl ether at 0° C. to 5° C. The reaction mixture is then subsequently stirred at room temperature for 16 hours, shaken with 20 ml of water and then with 50 ml of saturated sodium bicarbonate solution, dried over sodium sulphate and evaporated in vacuo. The residue is recrystallized from isopropanol.

7.2 g (44% of theory) of (5-dichloromethyl-1,3,4-thiadiazol-2-yl)-oxyacetic acid N-methylanilide are thus obtained in the form of beige crystals of melting point 114° C.

PREPARATION OF THE STARTING SUBSTANCE

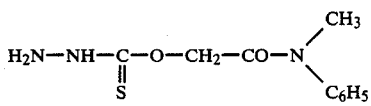

33 g (0.2 mole) of glycolic acid N-methylanilide are first added to a solution of 11.2 g (0.2 mole) of potassium hydroxide in 40 ml of water at 10° C., followed by 15.2 g (0.2 mole) of carbon disulphide. The mixture is subsequently stirred at 10° C. to 15° C. for 10 minutes and 23.2 g (0.2 mole) of sodium chloroacetate are added to the suspension thereby formed. The temperature of the reaction mixture rises to about 38° C. After 1 hour, 10 g (0.2 mole) of hydrazine hydrate are added dropwise at 5° C. to 10° C., with cooling, 100 ml of ice-water are added to the mixture and the mixture is extracted 3 times with 50 ml of chloroform each time.

After the solvent has been evaporated off, 43.2 g (90% of theory) of O-(N-methyl-N-phenylcarbamoyl-methyl) hydrazine-thiocarboxylate are obtained in the form of light grey crystals of melting point 113° C.

Example 4

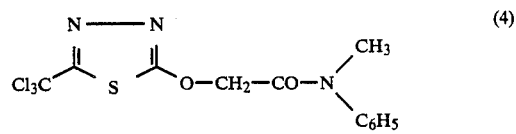

(Process (c))

11.5 g (0.03 mole) of O-(N-methyl-N-phenyl-carbamoyl-methyl) N'-trichloroacetyl-hydrazine-N-thiocarboxylate are added to 55 g of concentrated sulphuric acid at 0° C. to 10° C. The mixture is subsequently stirred at 0° C. to 10° C. for 2 hours, poured onto 200 g of ice-water and extracted twice with 50 ml of diethyl ether each time. The organic phases are shaken first with 20 ml of water and then with saturated sodium bicarbonate solution, dried over sodium sulphate and evaporated in vacuo. The residue is recrystallized from isopropanol.

3.9 g (36% of theory) of (5-trichloromethyl-1,3,4-thiadiazol-2-yl)-oxyacetic acid N-methylanilide are obtained in this manner in the form of colorless crystals of melting point 100° C.

PREPARATION OF THE STARTING SUBSTANCE

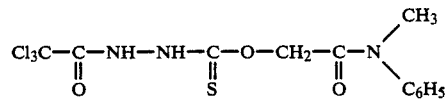

4 g (0.05 mole) of pyridine are first added to a mixture of 11.95 g (0.05 mole) of O-(N-methyl-N-phenylcarbamoylmethyl) hydrazine-thiocarboxylate and 25 ml of N,N-dimethylformamide at 0° C. to 5° C., followed by 9.1 g (0.05 mole) of trichloroacetyl chloride. The mixture is subsequently stirred at 0° C. to 5° C. for ½ hour and 100 ml of ice-water are then added. After crystallization, the reaction product which has precipitated is filtered off with suction.

14.8 g (77% of theory) of O-(N-methyl-N-phenylcarbamoylmethyl) N'-trichloroacetyl-hydrazine-N-thiocarboxylate are thus obtained in the form of a colorless powder of melting point 104° C. (decomposition).

The following 5-halogenoalkyl-1,3,4-thiadiazol-2-yloxyacetamides of the general formula (I) are obtained in a corresponding manner and in accordance with the general description of the preparation:

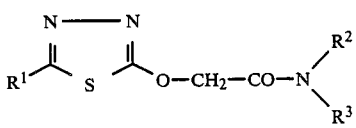

27.5%, boiling point; 74–75° C./22 mbar; $n_D^{20}$: 1.4890

6.5%, boiling point: 127° C. $n_D^{20}$: 1.4424

Remainder (2.9%): small amounts of several by-pro-

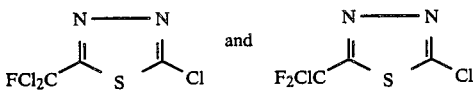

(I)

| Example No. | $R^1$ | $R^2$ | $R^3$ | Physical properties |
|---|---|---|---|---|
| 5 | ClF$_2$C— | CH$_3$ | C$_6$H$_5$ | $n_D^{20}$ 1.5450 |
| 6 | Cl$_2$CH— | n-C$_3$H$_7$ | n-C$_3$H$_7$ | $n_D^{25}$ 1.5142 |
| 7 | Cl$_2$CH— | C$_2$H$_5$ | C$_2$H$_5$ | $n_D^{20}$ 1.5215 |
| 8 | Cl$_2$CH— | CH$_2$=CH—CH$_2$— | CH$_2$=CH—CH$_2$— | melting point 53–56° C. |
| 9 | Cl$_2$CH— | —O—(CH$_2$)$_2$—OC$_2$H$_5$ | i-C$_3$H$_7$ | |
| 10 | Cl—CH$_2$— | CH$_3$ | C$_6$H$_5$ | melting point 108–110° C. |

PREPARATION OF FURTHER STARTING SUBSTANCES

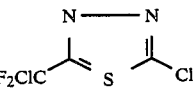

and

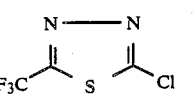

665 g of 2-chloro-5-trichloromethyl-1,3,4-thiadiazole (boiling point 82°–83° C./0.8 mbar; melting point 38°–40° C.) are initially introduced into a stainless steel stirred autoclave with a reflux condenser and pressure regulator. 2 liters of anhydrous hydrogen fluoride are allowed to run in at a temperature of about 0° C. and the autoclave is then closed. Nitrogen is forced in to a protective pressure of 10 bar and the mixture is then slowly heated up to 160° C.

The reaction starts at about 130°–140° C., which manifests itself in a significant increase in pressure. The hydrogen fluoride formed is let down continuously under 33 bar via the regulatory valve. As soon as the reaction subsides, the pressure is reduced slowly and continuously to 30 bar and the reaction is brought to completion under this pressure, under reflux conditions for the hydrogen fluoride. The autoclave is then cooled and let down and the excess hydrogen fluoride is removed by distillation. The residue is poured onto ice-water and the organic phase is separated off and dried over sodium sulphate. According to analysis by gas chromatography, the crude mixture has the following composition:

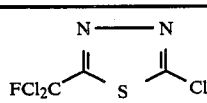

63.1%, boiling point: 101–103° C./22 mbar; $n_D^{20}$: 1.5312 ducts.

The compounds 2-chloro-5-fluorodichloromethyl-1,3,4-thiadiazole and 2-chloro-5-difluorochloromethyl-1,3,4-thiadiazole are obtained in a pure form by fractional distillation. These two compounds are new are likewise the subject of this invention.

USE EXAMPLES

The compounds shown below are used as comparison substances in the use examples which follow:

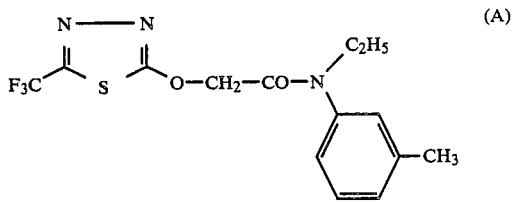

(A)

N-Ethyl-N-(3-methylphenyl)-5-trifluoromethyl-1,3,4-thiadiazol-2-yloxyacetamide

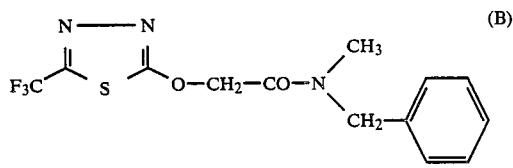

(B)

N-Benzyl-N-methyl-5-trifluoromethyl-1,3,4-thiadiazol-2-yloxyacetamide
(both known from DE-OS (German Published Specification) No. 3,218,482)

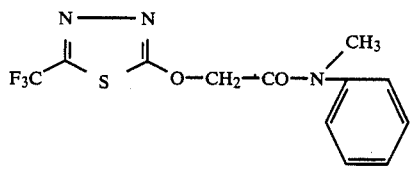
(C)

N-Methyl-N-phenyl-5-trifluoromethyl-1,3,4-thiadiazol-2-yloxyacetamide (known from DE-OS (German Published Specification) No. 3,004,326)

Example A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)

100% = total destruction

In this test, a clearly superior activity and crop plant selectivity compared with the prior art is shown, for example, by the compound according to preparation Example 3.

Example B

Puccinia test (wheat)/protective
Solvent: 100 parts by weight of dimethylformamide
Emulsifier: 0.25 parts by weight of alkylarylpolyglycolether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of Puccinia recondita in a 0.1% strength aqueous agar solution. After the spore suspension has dried on, the plants are sprayed with the preparation of active compound until dew-moist. The plants remain in an incubation cabinet at 20° and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compounds according to the following preparation examples: (3) and (4).

Example C

Pyricularia Test (rice)/protective
Solvent: 12,5 parts by weight of acetone
Emulsifier: 0,3 parts by weight of alkylarylpolyglycolether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried off, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: (3), (4).

Example D

Pyricularia Test (rice)/systemic
Solvent: 12,5 parts by weight of acetone
Emulsifier: 0,3 parts by weight of alkylarylpolyglycolether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples:

It is understood that the specification and examples are illustrative but not limitative of the present invention and that other embodiments within the spirit and scope of the invention will suggest themselves to those skilled in the art.

I claim:

1. A 2-chloro-5-trihalomethyl-1,3,4-thiadiazole of the formula

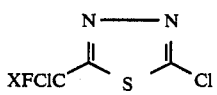

in which
X is F or Cl.

2. A compound according to claim 1, in which X is F.

3. A compound according to claim 1, in which X is Cl.

* * * * *

UNITED STATES PATENT AND TRADEMARK OFFICE
CERTIFICATE OF CORRECTION

PATENT NO. : 4,791,208

DATED : December 13, 1988

INVENTOR(S) : Heinz Förster, et al

It is certified that error appears in the above-identified patent and that said Letters Patent is hereby corrected as shown below:

| | |
|---|---|
| Col. 1, line 22 | Delete "DOS No. 3,004,326." and substitute --DOS No. 3,004,326).-- |
| Col. 3, line 2 | Delete "thiadiazol2-" and substitute -- -thiadiazol-2- -- |
| Col. 3, line 35 | Delete "1 to 2" and substitute --1 or 2-- |
| Col. 29, line 50 Formula (VII) | Delete "$R^1$" and substitute --$R^2$-- |
| Col. 30, line 42 | Delete "generally compounds" and substitute --generally known compounds-- |
| Col. 42, line 48 | After "following preparation examples:" insert -- (3) and (4) -- |

Signed and Sealed this

Twenty-sixth Day of December, 1989

Attest:

JEFFREY M. SAMUELS

Attesting Officer    Acting Commissioner of Patents and Trademarks